(12) United States Patent
Lucio et al.

(10) Patent No.: US 11,565,069 B2
(45) Date of Patent: Jan. 31, 2023

(54) MASK WITH ADHESIVE AND METHOD OF MAKING THE SAME

(71) Applicant: 3B Medical, Inc., Winter Haven, FL (US)

(72) Inventors: Albert A. Lucio, Haines City, FL (US); Angela Giudice, Kissimmee, FL (US)

(73) Assignee: 3B MEDICAL, INC., Winter Haven, FL (US)

( * ) Notice: Subject to any disclaimer, the term of this patent is extended or adjusted under 35 U.S.C. 154(b) by 542 days.

(21) Appl. No.: 15/821,194

(22) Filed: Nov. 22, 2017

(65) Prior Publication Data
US 2019/0105456 A1    Apr. 11, 2019

Related U.S. Application Data

(60) Provisional application No. 62/569,640, filed on Oct. 9, 2017.

(51) Int. Cl.
| | |
|---|---|
| *A61M 16/06* | (2006.01) |
| *A61M 16/08* | (2006.01) |
| *A62B 18/08* | (2006.01) |
| *A41D 13/11* | (2006.01) |

(52) U.S. Cl.
CPC .... *A61M 16/0688* (2014.02); *A61M 16/0605* (2014.02); *A61M 16/0825* (2014.02); *A41D 13/1169* (2013.01); *A41D 13/1176* (2013.01); *A62B 18/08* (2013.01)

(58) Field of Classification Search
CPC ........ A61M 16/00; A61M 16/06–0694; A61M 16/0003–0012; A61M 16/20–209; A61M 2016/0015–0042; A61M 16/0605; A61M 16/0688; A63B 11/12; A63B 11/18; A62B 7/00; A62B 7/04; A62B 7/14; A61B 9/00; A61B 9/02; A41D 13/1169
See application file for complete search history.

(56) References Cited

U.S. PATENT DOCUMENTS

| | | | |
|---|---|---|---|
| 3,020,260 A | 2/1962 | Nelson | |
| 3,556,097 A * | 1/1971 | Wallace | A61M 16/06 |
| | | | 128/202.23 |
| 5,901,707 A * | 5/1999 | Gonçalves | A61B 90/04 |
| | | | 128/849 |
| 5,918,598 A * | 7/1999 | Belfer | A41D 13/1176 |
| | | | 128/205.25 |
| 6,196,223 B1 * | 3/2001 | Belfer | A41D 13/1176 |
| | | | 128/205.25 |
| 6,846,508 B1 | 1/2005 | Colas et al. | |
| 7,077,138 B2 * | 7/2006 | Bateman | A61M 16/0463 |
| | | | 128/206.14 |

(Continued)

FOREIGN PATENT DOCUMENTS

| | | |
|---|---|---|
| EP | 0300620 A1 | 1/1989 |
| EP | 0322118 A1 | 6/1989 |

(Continued)

*Primary Examiner* — Samchuan C Yao

(74) *Attorney, Agent, or Firm* — Carlson, Gaskey & Olds, P.C.

(57) ABSTRACT

This disclosure relates to a mask which delivers pressurized airflow to a patient. The mask includes a central portion and a wing projecting from the central portion. The wing is configured to adhere to a patient's cheek.

22 Claims, 3 Drawing Sheets

(56) References Cited

U.S. PATENT DOCUMENTS

| | | | | |
|---|---|---|---|---|
| 7,255,107 B1 * | 8/2007 | Gomez | ............ | A61M 16/0666 |
| | | | | 128/206.11 |
| 2006/0096598 A1 * | 5/2006 | Ho | ........................ | A61M 16/06 |
| | | | | 128/206.24 |
| 2006/0237017 A1 * | 10/2006 | Davidson | .............. | A61M 16/06 |
| | | | | 128/205.25 |
| 2007/0169776 A1 * | 7/2007 | Kepler | .................. | A61M 16/16 |
| | | | | 128/200.23 |

FOREIGN PATENT DOCUMENTS

| | | |
|---|---|---|
| GB | 849885 | 9/1960 |
| GB | 945580 | 1/1964 |
| GB | 2192142 A | 1/1988 |

* cited by examiner

MASK WITH ADHESIVE AND METHOD OF MAKING THE SAME

RELATED APPLICATIONS

This application claims the benefit of U.S. Provisional Application No. 62/569,640 filed Oct. 9, 2017, the entirety of which is herein incorporated by reference.

BACKGROUND

This disclosure relates to a CPAP mask which incorporates adhesive to attach to a user.

Sleep apnea afflicts millions of people in the United States. It occurs when a person's tongue or soft palette relaxes during sleep, closing off the breathing passage. The interrupted flow of oxygen and disrupted sleep pattern that results have serious ramifications. It makes people perpetually tired. It can cause a drop in blood oxygen levels, which strain the respiratory and circulatory system. It causes high blood pressure and cardiovascular disease. It also impacts the afflicted sleeper's partner, who suffers from listening to the resulting snoring and worrying about the sleeper's irregular breathing pattern—including episodes when the sleeper stops breathing.

Continuous positive airway pressure (or CPAP) therapy systems are commonly used to help people with sleep apnea breathe more easily during sleep. CPAP therapy systems increase air pressure in a patient's throat so that their airway does not collapse as they breathe in. CPAP therapy systems consist of (1) a flow generator for creating the flow of air, (2) a conduit—typically a heated or insulated hose or other flexible connector—for carrying the air to the patient, and (3) an interface—such as a mask, together with equipment that secures it to the patient's head—for delivering the pressurized air to the patient's airway.

Traditionally, headgear has been required to secure the mask to the patients head. The headgear typically attaches to the mask and wraps around a patients head. Some patients may find headgear to be cumbersome and uncomfortable while trying to sleep. Further, the headgear fixation method is not desirable in many situations. For example, it may be very difficult to fit pediatric patients with headgear.

There is also a need for a disposable, single-use CPAP mask. In a hospital setting, patients waiting for surgery are often fitted with a CPAP mask that is later discarded after the patient's discharge. Additionally, a disposable CPAP mask may be desirable for use in sleep studies, where titration is performed to determine the optimal CPAP pressure setting required to resolve a patient's apnea episodes.

SUMMARY

This disclosure relates to a system and a mask to deliver pressurized airflow to a patient. The mask includes a central portion and a wing projecting from the central portion. The wing is configured to adhere to a patient's cheek.

A method of manufacturing a mask includes providing a mold for a mask. A soft elastomer compound is injected into the mold to form an initial structure of the mask. An adhesive gel is injected into the mold, and is molded to the surface of the initial structure.

BRIEF DESCRIPTION OF THE DRAWINGS

In FIG. 2A the conduit is not attached to the mask.

In FIG. 2B the conduit is attached to the mask.

DETAILED DESCRIPTION

This disclosure relates to a CPAP mask which incorporates an adhesive to attach the mask to a user's head, and in particular to a user's face. The disclosed mask provides a reliable and easy-to-use interface for use in a CPAP therapy system. To attach the disclosed mask, a patient simply orients the mask in the appropriate position, and applies pressure to the mask, thereby causing the adhesive to bond to the patient's face. The adhesive secures the mask to the patient's skin without the need of headgear. The mask retains an appropriate air seal even when the patient lies on his or her side. The mask may be relatively inexpensively made, making it suitable for one-time use applications. In some examples the mask may be reusable, while in other examples the mask is intended to be disposable. As will be appreciated, the mask is particularly useful in neonatal applications, in particular because it may be difficult to affix traditional CPAP headgear to infants.

Figure 1:
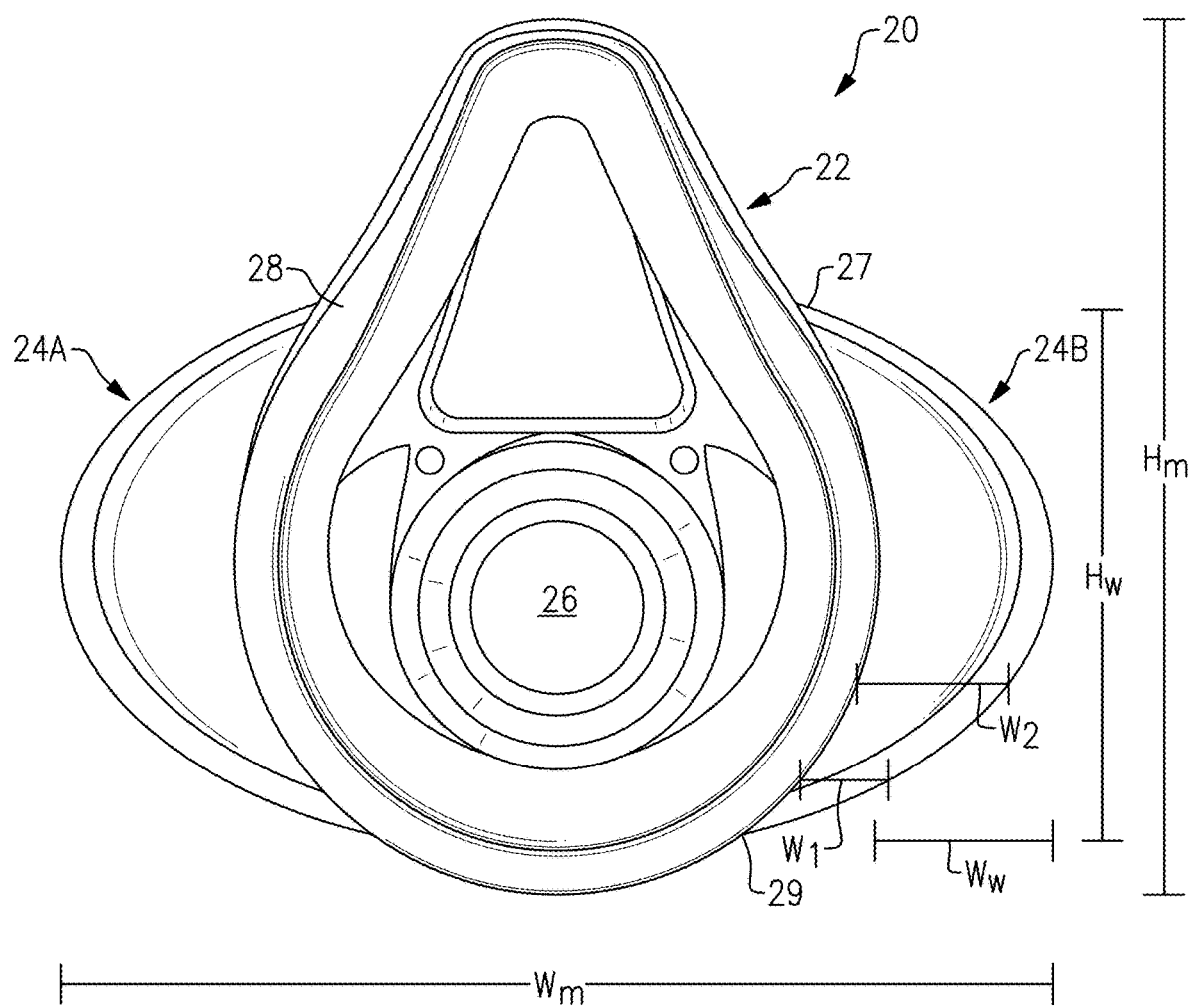
FIG. 1 is a rear view of an example mask.
Figure 3:
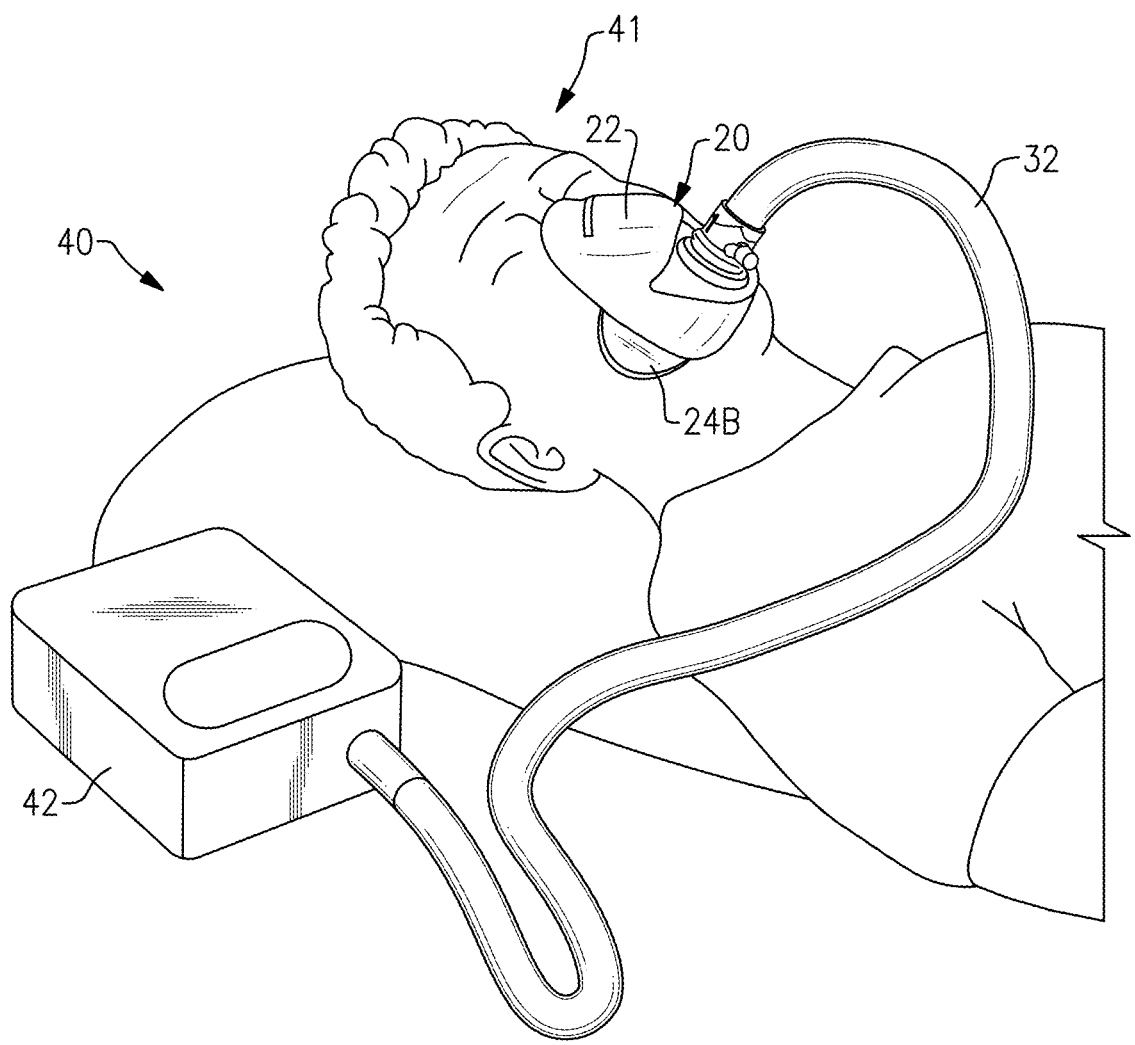
FIG. 3 illustrates a CPAP therapy system incorporating the mask of FIG. 1.

FIG. 1 illustrates an example mask 20 for use with a CPAP therapy system, such as that shown in FIG. 3. The mask 20 consists of a central portion 22 which is configured to surround a patient's mouth and nose, and two wings 24A, 24B, which project from opposite sides of the central portion 22 and are configured to adhere to a patient's lower cheek area. While the central portion 22 is configured to surround both the mouth and the nose of the patient in this example, the central portion 22 may be configured to surround only a mouth or a nose in other examples. The mask 20 further includes an aperture 26 configured to receive a conduit for delivering airflow. In one example, a rim 28 of the central portion 22 and the wings 24A, 24B are partially formed of an adhesive material. In another embodiment, the rim 28 is not made of adhesive material, and only the wings 24A, 24B are partially formed of adhesive material. In still another embodiment, the wings 24A, 24B are entirely formed of adhesive material.

A certain amount of adhesive contact area is required to maintain an air seal if the patient is a side sleeper. Patients have limited comfort tolerances relating to the size and location of the adhesive material affecting their skin. Particularly, patient sensitivity is typically greatest around the nose and lip. Widened adhesive contact in these sensitive areas may cause patient discomfort. Accordingly, wings 24A, 24B are provided to increase seal adhesion area in areas of the face where patients would experience the least sensitivity.

In one example of this disclosure, in order to facilitate appropriate seal adhesion while minimizing patient discomfort, the wings 24A, 24B are substantially crescent-shaped. That is, with reference to the wing 24B, the wings have a height $H_w$ extending between first and second ends 27, 29. The width of the wings is defined in this disclosure as the dimension perpendicular to the height $H_w$ of the wing. In the example of FIG. 1, the wings 24A, 24B are crescent-shaped, and thus the width of the wings taper toward the ends 27, 29. In particular, with reference to the wing 24B, the wing has a first width $W_1$ adjacent the end 29, and has a second, larger width $W_2$ moving away from the end 29. The wings have a maximum width $W_w$ between the ends 27, 29. It should be understood that the wings 24A, 24B are arranged substantially the same way and, in particular, are generally symmetrical.

In addition to the crescent-shape of the wings 24A, 24B, the height of the wings 24A, 24B is optimized for comfort and adhesion. In one example of this disclosure, the wings 24A, 24B have a height $H_w$, which is controlled relative to the total height of the mask $H_m$. In one example, the ratio of $H_w/H_m$ is between about 0.5 and 0.7. In a more particular embodiment, the ratio is between about 0.55 and 0.65. In an even more particular example, the ratio is about 0.59.

As mentioned above, the wings 24A, 24B are substantially crescent-shaped. In order to optimize the width of the wings 24A, 24B for comfort and adhesion, the maximum width $W_w$ of the wings 24A, 24B is controlled relative to the total width of the mask $W_m$. In one example, the ratio of $W_w/W_m$ is between about 0.1 and 0.3. In a more particular example, the ratio is between about 0.15 and 0.25. In an even more particular example, the ratio is about 0.175.

While wings 24A, 24B extend over the lower cheek area in the illustrated embodiment, it should be understood that the wings 24A, 24B may also extend over other portions of the face. That said, the lower cheek area, which is beneath the orbit and to the side of the mouth, is relatively less sensitive to the application and removal of adhesive material. Further, while various ratios have been discussed above, those ratios may be used to produce masks in a variety of different sizes. For instance, the mask 20 may be sized for use with neonatal and pediatric patients, as well as adult patients. While the mask 20 is intended to eliminate the need for headgear, a simple elastic strap may be provided to apply minimal pressure on the mask 20 and reduce seal separation when a patient turns on their side.

Figure 2:
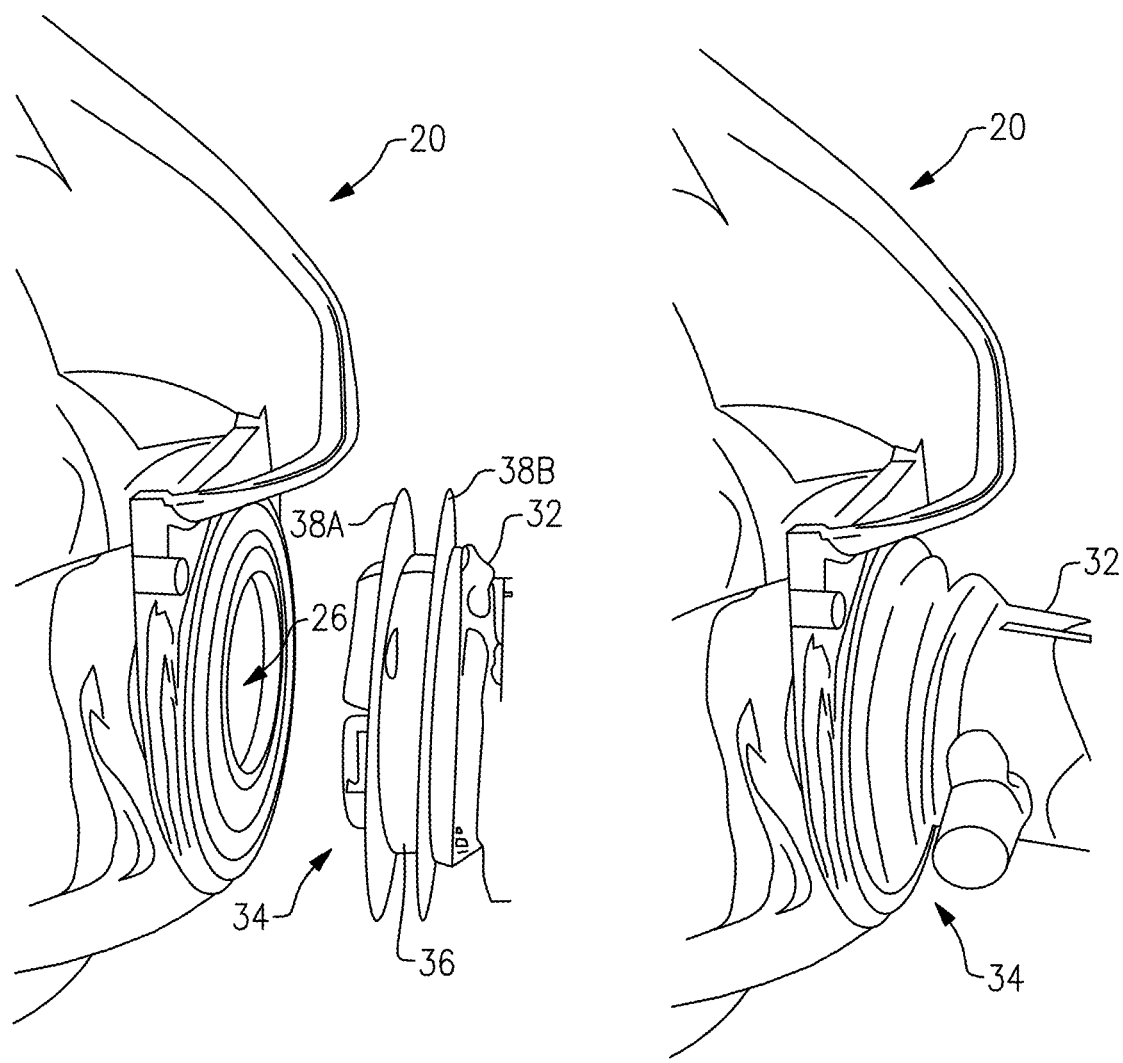
FIG. 2A illustrates the mask of FIG. 1 in a front-perspective view with a conduit attachment.
FIG. 2B illustrates the mask of FIG. 1 in a front-perspective view with a conduit attachment.

FIGS. 2A and 2B illustrate a perspective view of mask 20 with conduit attachment 32. Conduit 32 is typically an insulated hose or other flexible connector capable of communicating airflow from a flow generator to the mask 20. The conduit 32 may be formed of hard silicone. The conduit 32 includes a distal end 34 comprising a channel 36 and two parallel circular ridges 38A, 38B.

As illustrated in FIG. 2B, the distal end 34 of the conduit 32 is configured to attach to the mask 20 at the aperture 26. Circular ridge 38A is inserted through the aperture 26, and channel 36 is position within and proximate to the aperture 26. Accordingly, ridges 38A, 38B straddle aperture 26 and create an air seal between the conduit 32 and mask 20. Traditionally, CPAP masks have required a hard frame in order to interface with a conduit and form an air seal. Advantageously, the above described configuration generates an air seal without requiring a hard plastic frame on the mask, and allows the mask 20 to be made entirely of soft silicone.

FIG. 3 illustrates a CPAP therapy system 40 incorporating the mask 20. The system 40 includes a flow generator 42, conduit 32, and mask 20. To use the system 40, a patient 41 simply positions the central portion 22 of mask 20 around their mouth and nose and then applies pressure to the adhesive material located around the periphery of the central portion 22 and wings 24A, 24B. The conduit 32 may be attached to mask 20 prior to or after positioning the mask 20 on the patient's face. The flow generator 42 is then activated and pressurized airflow is delivered through the conduit 32 and into the air-sealed mask 20. The patient then inhales this pressurized air through the mask 20, which prevents the patient's airways from collapsing.

In one example of this disclosure, the mask 20 is made entirely of silicone, or another type of soft elastomer. Certain portions of the mask 20 are formed at least partially of adhesive material, such that those portions of the mask 20 can be adhered to a patient's skin. Example portions of the mask include the wings 24A, 24B and rim 28. In one example, the adhesive material consists of a two compound silicone elastomer that cross-links at room temperature. A cross-link is a bond that links one polymer chain to another, and generally promotes a difference in the polymers' physical properties. Accordingly, the cross-linking reaction may be used to produce a gel with appropriate tact and other desirable attributes.

In one example method of making the mask 20, the fabrication of the mask 20 occurs in a two shot or two-part molding process. In a first step, at least a majority of the central portion 22 is molded of a first silicone material. In a second step, the above-discussed adhesive material is molded over material injected during the first step. In one example, the adhesive material partially forms the wings 24A, 24B and the rim 28. In another example, the adhesive material partially forms only the wings 24A, 24B, and the rim 28 is entirely formed in the first step. In this process, molding of mask 20 involves a multi-material injection molding (MMM) process that allows the initial silicone structure to mix and mold before a second mix of liquid silicone adhesive material is molded to the surface of the structure.

In another example of making the mask 20, the adhesive material is manually provided in a separate step after the molding of the initial mask structure. In this example, an adhesive gel is encased on two sides with a peel-off material and is die cut to shape the mask 20. The peel-off material is removed on one side of the gel, and that side is applied to the mask. The other peel-off portion is left on until the mask is applied to a patient.

The adhesive material may be formed from linear or branched silicones having reactive groups that undergo a crosslinking reaction during curing. Examples of crosslinking reactions include the hydrosilylation reaction in which a silicone having an Si—H reactive group reacts with a silicone having an aliphatically unsaturated reactive group in the presence of a platinum or rhodium catalyst. Alternatively, the reaction can involve the reaction of a silicone having an Si—OH reactive group with a silicone or a chain extender (e.g., a silane) having an alkoxy reactive group in the presence of a metal catalyst. In yet another alternative embodiment, a silicone having an Si—OH containing polymer is mixed with an alkoxysilane in the presence of a titanate catalyst.

Other components can be included in the gel adhesive of the present invention, including but not limited to, fillers, pigments, low temperature cure inhibitors, additives for improving adhesion, pharmaceutical agents, cosmetic agents, resins, fluids or other materials conventionally used in gels.

The adhesive material is reusable and repositionable on the patients face while retaining its sticking strength. The adhesive material, in one example, has enough tack to support the weight of the mask 20 and attached conduit 32. In this example, the adhesive material is provided integrally with the remainder of the mask 20, and is not provided by a strip or pad of adhesive.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A mask configured to deliver pressurized airflow, comprising:
a central portion;
a wing projecting from the central portion, the wing configured to adhere to a patient's cheek, wherein the wing is at least partially provided by an adhesive material;
wherein the wing and central portion are molded together such that the adhesive material is provided integral with the mask;
wherein the central portion is configured to surround a patient's nose such that the mask is configured to deliver pressurized airflow to the patient's airways by delivering pressurized airflow into at least the patient's nostrils;
wherein the wing has a height between first and second ends;
wherein the wing is substantially crescent-shaped such that the wing has a width having a maximum width between the first and second ends and such that the width is tapered and gradually reduces from the maximum width to a point at each of the first and second ends; and
wherein the height of the wing is greater than the width of the wing.

2. The mask of claim 1, wherein the wing is one of a first wing and a second wing projecting from opposite sides of the mask.

3. The mask of claim 1, wherein a ratio of the height of the wing to a height of the central portion is between about 0.5 and 0.7.

4. The mask of claim 3, wherein the ratio of the height of the wing to the height of the central portion is between about 0.55 and 0.65.

5. The mask of claim 1, wherein a ratio of the maximum width of the wing to an overall width of the mask is between about 0.1 and 0.3.

6. The mask of claim 5, wherein the ratio of the maximum width of the wing to the overall width of the mask is between about 0.15 and 0.25.

7. The mask of claim 1, further comprising:
an aperture configure to receive a conduit for delivering airflow.

8. The mask of claim 1, wherein a rim of the central portion is at least partially provided by the adhesive material.

9. The mask of claim 1, wherein the adhesive material is a two compound silicone elastomer.

10. The mask of claim 1, wherein the adhesive material is not provided by a strip or a pad of adhesive.

11. The mask of claim 1, wherein the central portion is configured to surround the patient's mouth and nose.

12. The mask of claim 11, wherein the mask is configured to deliver pressurized airflow to the patient's airways by delivering pressurized airflow into both the patient's mouth and the patient's nostrils.

13. The mask of claim 1, wherein the wing converges with the central portion at the first and second ends.

14. The mask of claim 1, wherein the points at the first and second ends are provided by an intersection of a profile of the central portion with a profile of the wing.

15. A system for delivering pressurized airflow comprising:
a flow generator configured to output a pressurized airflow;
a conduit in fluid communication with the flow generator;
a mask in fluid communication with the conduit;
wherein the conduit is configured to deliver the pressurized airflow from the flow generator to the mask;
the mask comprising:
a central portion;
an aperture configured to receive the conduit;
a wing projecting from the central portion, the wing configured to adhere to a patient's cheek, wherein the wing is at least partially provided by an adhesive material, and wherein the wing is substantially crescent-shaped such that a height of the wing is greater than a width of the wing;
wherein the wing and central portion are molded together such that the adhesive material is provided integral with the mask; and
wherein the central portion is configured to surround a patient's nose such that the mask is configured to deliver pressurized airflow to the patient's airways by delivering pressurized airflow into at least the patient's nostrils.

16. The system of claim 15, wherein the mask is formed entirely of soft silicone.

17. The system of claim 16, wherein the conduit includes a distal end comprising a channel and two parallel circular ridges, and the distal end of the conduit is configured to attach to the mask at the aperture with the circular ridges straddling the aperture and the channel positioned within and proximate to the aperture.

18. The system of claim 15, wherein a ratio of a height of the wing to a height of the central portion is between about 0.5 and 0.7, and wherein the wing has a maximum width, a ratio of the maximum width of the wing to an overall width of the mask is between about 0.1 and 0.3.

19. The system of claim 15, wherein the adhesive material is a two compound silicone elastomer and is provided integral with the mask.

20. A method of manufacturing a mask, comprising:
injecting a soft elastomer compound into a mold to form an initial structure of the mask;
wherein the initial structure of the mask includes a central portion;
wherein the initial structure further includes at least a portion of a wing having a substantially crescent-shape such that a height of the wing is greater than a width of the wing, wherein the wing projecting from the central portion, the central portion configured to surround a patient's nose such that the mask is configured to deliver pressurized airflow to the patient's airways by delivering pressurized airflow into at least the patient's nostrils; and
providing an adhesive gel on the surface of the initial structure.

21. The method of claim 20, wherein the adhesive gel is injected into the mold and is molded to the surface of the initial structure.

22. The method of claim 20, wherein the adhesive gel is provided by:
   encasing the gel adhesive in a peel-off material;
   die cutting the gel adhesive to shape the mask; and
   removing a portion of the peel off material and attaching the gel adhesive to the mask.

\* \* \* \* \*